United States Patent [19]
DiBenedetto

[11] Patent Number: 5,486,157
[45] Date of Patent: Jan. 23, 1996

[54] DYNAMIC MULTI-ANGULAR ANKLE AND FOOT ORTHOSIS DEVICE

[76] Inventor: Anthony DiBenedetto, 7306 Yellow Creek Dr., Poland, Ohio 44514

[21] Appl. No.: 353,089

[22] Filed: Dec. 9, 1994

Related U.S. Application Data

[63] Continuation-in-part of Ser. No. 190,985, Feb. 3, 1994, abandoned.

[51] Int. Cl.⁶ .................................................. A61F 5/00
[52] U.S. Cl. ............................. 602/27; 602/16; 602/28
[58] Field of Search ............................... 602/5, 16, 23, 602/27–29; 128/882

[56] References Cited

U.S. PATENT DOCUMENTS

| | | |
|---|---|---|
| D. 297,368 | 8/1988 | Womack . |
| 3,345,654 | 10/1967 | Noble .................................. 602/28 X |
| 3,695,255 | 10/1972 | Rodgers et al. . |
| 3,976,059 | 8/1976 | Lonardo ................................ 602/28 |
| 4,192,502 | 3/1980 | Owen . |
| 4,289,122 | 9/1981 | Mason et al. . |
| 4,314,411 | 2/1982 | Hanson . |
| 4,371,160 | 2/1983 | Shooltz . |
| 4,379,370 | 4/1983 | Balbinot . |
| 4,454,871 | 6/1984 | Mann et al. . |
| 4,497,314 | 2/1985 | Miller . |
| 4,665,904 | 5/1987 | Lerman . |
| 4,718,179 | 1/1988 | Brown . |
| 4,753,229 | 6/1988 | Sutherland . |
| 4,817,589 | 4/1989 | Wertz . |
| 4,832,010 | 5/1989 | Lerman . |
| 4,869,001 | 9/1989 | Brown . |
| 5,020,523 | 6/1991 | Bodine ................................... 602/27 |
| 5,038,762 | 8/1991 | Hess et al. . |
| 5,044,360 | 9/1991 | Janke . |
| 5,086,760 | 2/1992 | Neumann et al. ................... 602/27 |
| 5,088,479 | 2/1992 | Detoro . |
| 5,151,081 | 9/1992 | Williams .............................. 602/27 |
| 5,154,695 | 10/1992 | Farris et al. ......................... 602/27 |
| 5,215,508 | 6/1993 | Bastow ............................. 602/27 X |
| 5,219,324 | 6/1993 | Hall . |
| 5,224,925 | 7/1993 | Varn .................................... 602/28 |
| 5,234,230 | 8/1993 | Crane et al. . |
| 5,269,748 | 12/1993 | Lonardo . |

OTHER PUBLICATIONS

Literature on "L.S.U. Lively Orthosis".

*Primary Examiner*—Linda C. Dvorak
*Attorney, Agent, or Firm*—Fay, Sharpe, Beall, Fagan, Minnich & McKee

[57] ABSTRACT

A substantially L-shaped orthopedic brace having a posterior upright that attaches at one end to a thermoplastic calf plate and at the other end to a thermoplastic foot plate. The brace further comprises a hinge at the apex of a contoured heel portion of the upright to provide dorsiflexion and plantar flexion, and a pivot point located below the hinge to provide inversion, eversion, pronation, and supination of the foot. Straps are also provided to attach the calf plate to the foot plate. Leverage bars connect the straps to the foot plate.

14 Claims, 5 Drawing Sheets

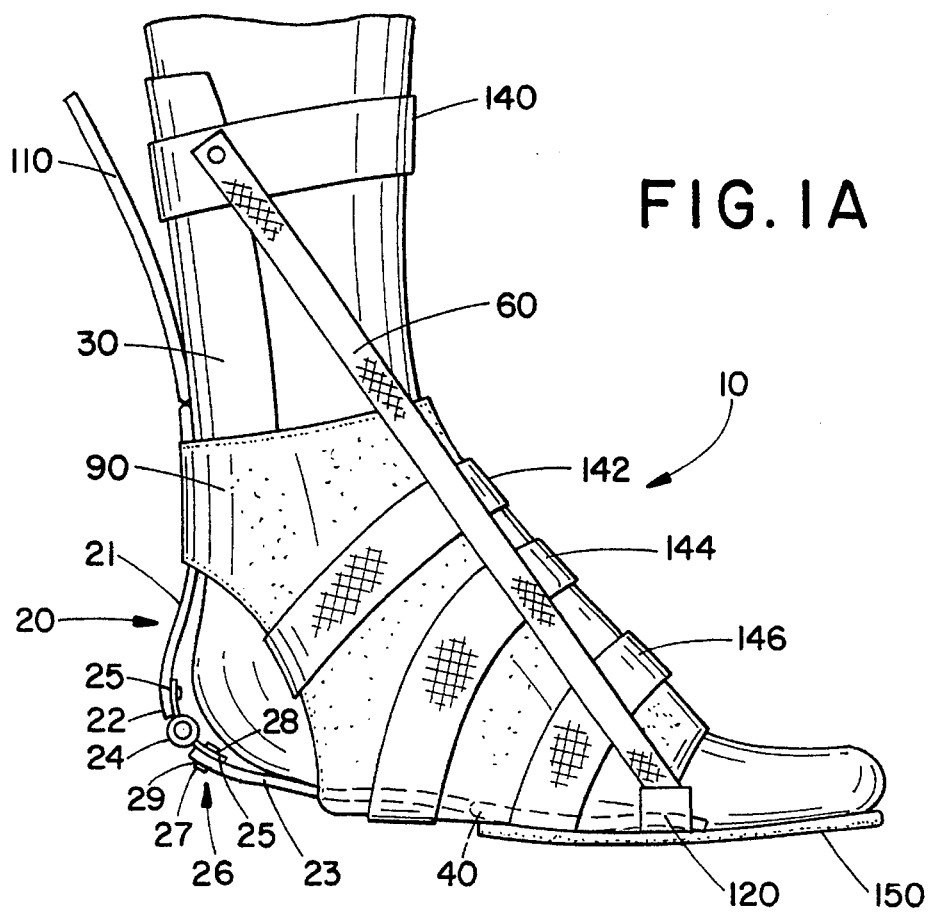
FIG. 1A
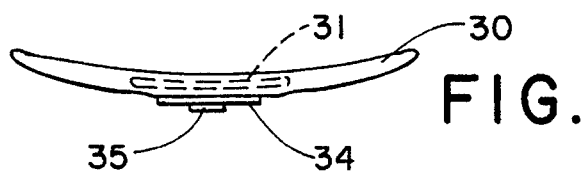
FIG. 2C
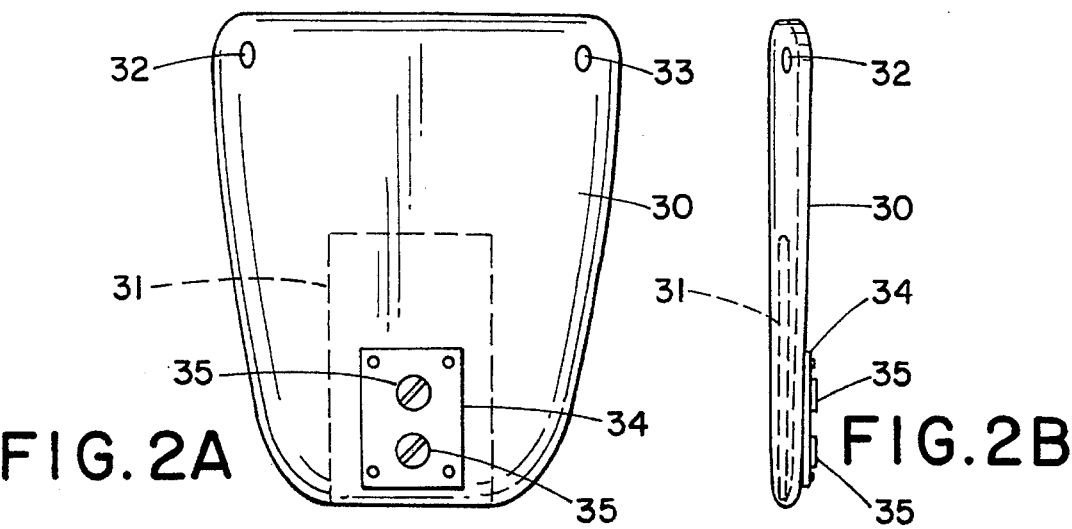
FIG. 2A
FIG. 2B

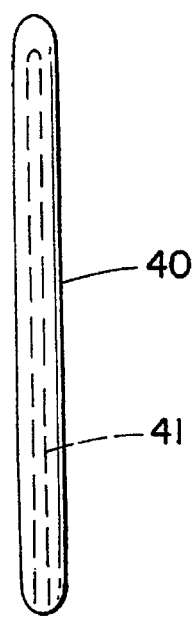
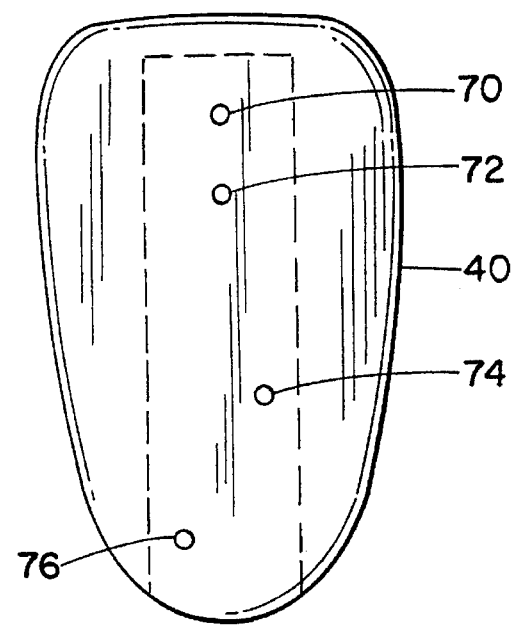
FIG. 3B  FIG. 3A
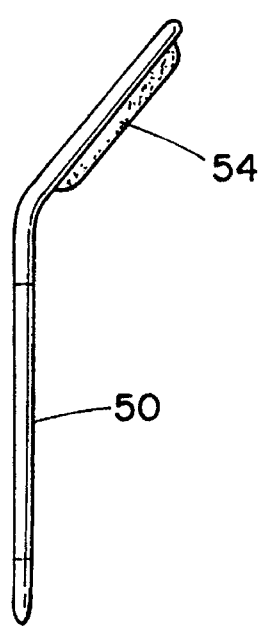
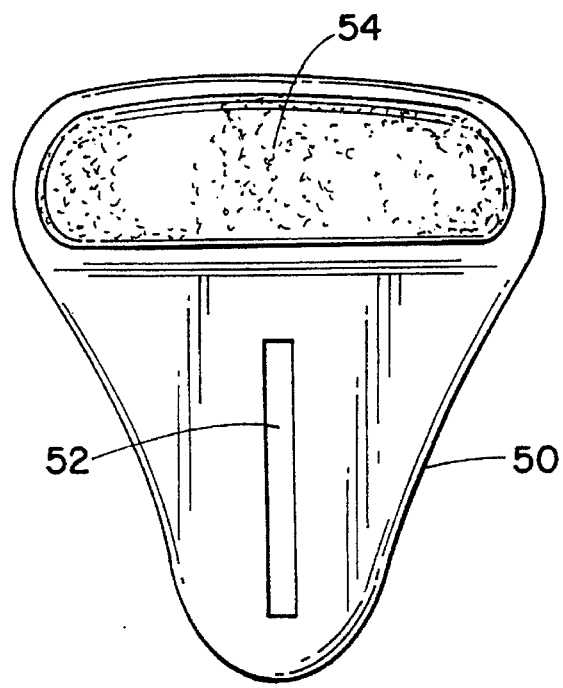
FIG. 4B  FIG. 4A 5,486,157

DYNAMIC MULTI-ANGULAR ANKLE AND FOOT ORTHOSIS DEVICE

This application is a continuation-in-part application of application Ser. No. 08/190,985, filed Feb. 3, 1994, now abandoned.

BACKGROUND OF THE INVENTION

This invention relates to a device designed for treatment and/or prevention of abnormalities of the ankle and foot complex. More particularly, the invention is directed to a substantially L-shaped orthopedic brace having a posterior upright that attaches at one end to a thermoplastic calf plate and at the other end to a thermoplastic foot plate. The brace further comprises a hinge at the apex of a contoured heel portion of the upright to provide free dorsiflexion and plantar flexion, and a pivot point located below the hinge to advantageously provide free inversion, eversion, pronation, and supination of the foot. Straps are also provided to attach the proximal end of the calf plate to leverage bars of the distal end of the foot plate. Proximal and distal are referenced herein as being relative to any part of the human body spaced from the ankle and foot complex while the body is in a standing position including, for example, the knee or head.

While the invention is particularly directed to the art of ankle and foot orthosis devices, and will be thus described with specific reference thereto, it will be appreciated that the invention may have usefulness in other fields and applications.

A wide variety of ankle and foot orthosis devices are known. However, those known lack a number of convenient features incorporated in the present invention.

For instance, U.S. Pat. No. 5,088,479 to Detoro is directed to an ankle and foot orthosis device for use in support, protection and partial immobilization of the ankle and foot complex. However, the Detoro patent does not teach the provision of a hinge, for facilitation of free dorsiflexion and plantar flexion, or a pivot point, for facilitation of free inversion, eversion, pronation, and supination. Moreover, the Detoro patent does not disclose the use of straps extending from the calf plate to the foot plate of the device nor leverage bars for connecting the straps to the foot plate.

Additionally, U.S. Pat. No. 4,289,122 to Mason, et al. is directed to an ankle-foot orthosis device which comprises a foot section and a leg section articulately attached to one another to provide dorsiflexion and limited plantar flexion. U.S. Pat. No. 4,665,904 to Lerman is directed to a preventive brace which includes circular hinges allowing rotation of a leg supporting shell with respect to a foot supporting shell. U.S. Pat. No. 5,044,360 to Janke is directed to an orthosis device with variable motion control and includes cam members which selectively provide different angles of rotation in plantar flexion and dorsiflexion. None of these patents, however, specifically teach a pivot point which allows inversion, eversion, supination, and pronation. Further, these patents fail to disclose use of straps which attach at the proximal end of the calf plate and the distal end of the foot plate. Consequently, leverage bars facilitating attachment of the straps to the foot plate are not shown.

Moreover, U.S. Pat. No. 4,817,589 to Wertz is directed to a foot support device adapted to engage a posterior ankle section of a leg having a strap means for providing dorsiflexion and eversion assistance, the strap means being connected to the support member and attached to predetermined points on a shoe. The Wertz patent, however, does not disclose a foot brace comprising an upright, a calf plate and a foot plate and, consequently, does not teach the use of a hinge and a screw incorporated into the upright to facilitate multiangular movement of the ankle and foot complex. Moreover, the Wertz patent does not disclose use of leverage bars facilitating attachment of the straps.

U.S. Pat. No. 5,086,760 to Neumann et al. relates to an articulated orthotic brace for an anatomical joint. The Neumann patent, however, discloses a device having motion limitations set by a screw which can be tightened. The Neumann patent does not disclose a device allowing dynamic unrestricted motion facilitated by a combination of the free motion of the joint itself and stored energy within associated elastic straps. Moreover, the Neumann patent shows two (2) ankle joints, one on each side of the ankle attached to two (2) uprights that are placed near the anatomical axis of rotation, if aligned properly.

SUMMARY OF THE INVENTION

An object of the present invention is to provide a dynamic multi-angular ankle and foot orthosis device which allows for free dorsiflexion, plantar flexion, inversion, eversion, supination and pronation of the ankle and foot complex.

A further object of the present invention is the provision of a dynamic multi-angular ankle and foot orthosis device including a toe extension plate adjustably connected to a foot plate, the toe extension plate providing a surface area for placement of the toes or to keep bed sheets from contacting hypersensitive toes.

A still further object of the present invention is the provision of a dynamic multi-angular ankle and foot orthosis device including an enclosable adjustable foot boot attached to the foot plate for securing the device to the ankle and foot complex wherein the boot comprises a vinyl and lambs wool base with a plurality of hook and loop fasteners attached thereto.

Yet another object of the present invention is to provide a dynamic multi-angular ankle and foot orthosis device incorporating straps suitably attached to both the foot plate and the calf plate to exert sufficient force to dorsiflex pronate, and supinate a foot.

A still further object of the present invention is the provision of a dynamic multi-angular ankle and foot orthosis device including leverage bars attached to the foot plate for securing the straps to the foot plate.

A still further object of the present invention is the provision of a dynamic multi-angular ankle and foot orthosis device which includes a derotation bar connected to the calf plate for controlling rotation of the lower extremity, i.e. rotation originating in the hip.

A still further object of the present invention is the provision of a calf plate slide attachment assembly.

The above objects are achieved in the present invention by providing a dynamic multi-angular ankle and foot orthosis device which comprises an orthopedic brace designed for treatment and/or prevention of abnormalities of the ankle and foot complex. The device utilizes a substantially L-shaped posterior upright that attaches at a proximal end to a thermoplastic calf plate and at a distal end to a thermoplastic foot plate. Adjustability for length at both ends can be easily achieved, particularly by the calf plate end which includes an adjustable calf plate slide attachment assembly.

Incorporated into the design is a high density lambs wool or equivalent foot boot that maintains optimal positioning of the human foot against the device. On the proximal portion of the thermoplastic calf plate is a padded hook and loop fastener closure used to maintain the calf component to the leg. On the middle posterior portion of the calf component, an aluminum deroration bar is provided which pivots 180 degrees for control of internal or external rotation of the lower extremity of the user.

The posterior upright extends through nearly the full length of the foot plate. The upright is hinged at the apex of the heel contour to allow free dorsiflexion and plantar flexion. Below the hinge is a pivot point that allows free inversion, eversion, pronation, and supination of the foot.

Furthermore, attached to the distal end of the foot plate, are leverage bars that extend laterally from the foot plate for increased leverage and serve as an attachment point for straps. The proximal attachments of the straps utilize an adjustable clip attached through the same holes used for the hook and loop closure for independent tension settings thereof.

The present invention allows for the treatment and/or prevention of contractures and other abnormalities of the ankle and foot complex by utilization of free motion in conjunction with the straps. Additionally, inherent to the design is the ability to suspend the patient's heel thus preventing any type of pressure sores from prolonged contact with bedding.

Further scope of the applicability of the present invention will become apparent from the detailed description provided below. It should be understood, however, that the detailed description and specific examples, which indicate preferred embodiments of the invention, are given by way of illustration only, since various changes and modifications within the spirit and scope of the invention will become apparent to those skilled in the art.

DESCRIPTION OF THE DRAWINGS

The present invention exists in the construction, arrangement, and combination of various parts of the device, whereby the objects contemplated are attained as hereinafter more fully set forth, specifically pointed out in the claims, and illustrated in the accompanying drawings in which:

FIG. 1a is a side elevational view of the dynamic multi-angular ankle and foot orthosis device;

FIG. 1b is a back elevational view of the calf plate and calf section of the device of FIG. 1a;

FIG. 2a is a rear elevational view of the calf plate of the device of FIG. 1;

FIG. 2b is a side elevational view of the calf plate shown in FIG. 2a;

FIG. 2c is a top plan view of the calf plate shown in FIG. 2a;

FIG. 3a is a top plan view of the foot plate of the device of FIG. 1;

FIG. 3b is a side elevational view of the foot plate shown in FIG. 3a;

FIG. 4a is a top plan view of the toe extension plate of the device of FIG. 1;

FIG. 4b is a side elevational view of the toe extension plate show in FIG. 4a;

FIG. 7a is a bottom plan view of the foot plate of the device of FIG. 1 incorporating leverage bars; and, FIG. 7b is a side elevational view of the foot plate shown in FIG. 7a.

DETAILED DESCRIPTION OF THE PREFERRED EMBODIMENTS

Figure 1B:
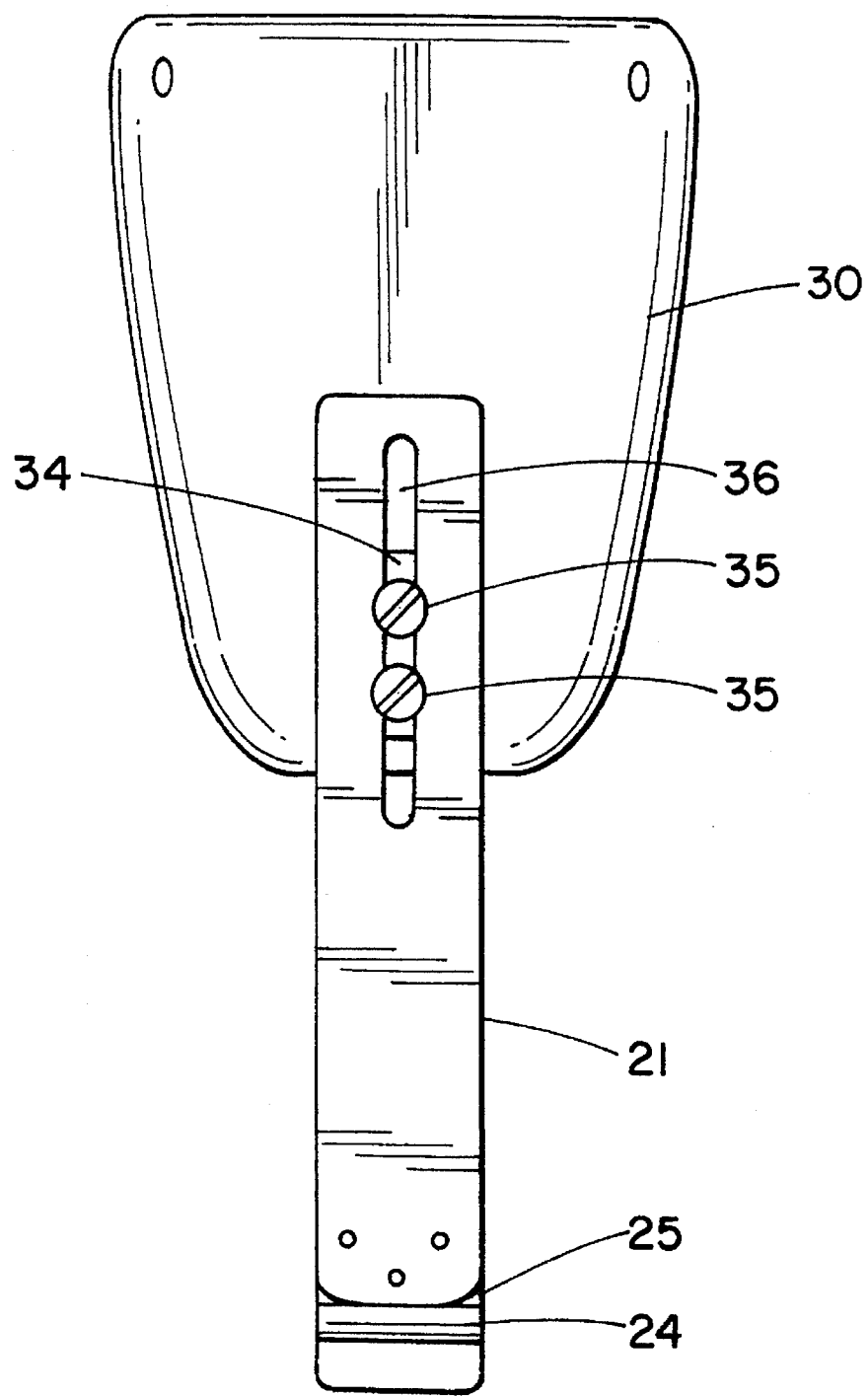

Referring now to the drawings wherein the showings are for purposes of illustrating the preferred embodiments of the invention only and not for purposes of limiting same, FIG. 1a provides a view of the overall preferred embodiment. As shown, the dynamic multi-angular ankle and foot orthosis device 10 is comprised of a substantially L-shaped posterior upright 20 having a calf section 21 and a foot section 23. A calf plate 30 is attached at a proximal end of the calf section 21 of the upright 20 and a foot plate 40 is connected to the distal end of the foot section 23 of the upright 20. Additionally, a toe extension plate 50 is connected to the foot plate 40 while straps 60 and 62 (not shown) connect the foot plate 40 to the calf plate 30. Leverage bars 120 and 122 (not shown) connect the straps 60 and 62 to the foot plate 40, respectively, and a foot boot 90 utilizes belts 142, 144 and 146. The upright 20 comprises a contoured heel portion 22. The heel portion 22 includes a hinge 24. A pivot point, or pivoting member, 26 is provided below the hinge 24 at approximately a 45° angle bisecting the L-shaped upright 20.

The hinge 24 and the pivot point 26 serve to provide multi-angular movement of the ankle and foot complex. More particularly, the hinge 24 is provided to an apex of the heel portion 22 to facilitate dorsiflexion and plantar flexion. The hinge 24 is connected to calf section 21 by pins, screws, bolts, or the like, in conjunction with hinge extension 25. The hinge 24 may also be integral with the calf section 21. The hinge 24 may be of any type well known to those skilled in the art. Furthermore, any type of component providing the aforementioned movement is recognized as being desirable to achieve the objects of the invention.

The pivot point 26 preferably comprises a screw 27 which engages corresponding openings 28 and 29 in overlapping hinge extension 25 and foot section 23, respectively. This arrangement facilitates free supination, pronation, inversion and eversion by allowing the calf section 21 and the foot section 23 to rotate about the screw 27 with respect to one another. It will be appreciated that still other pivot members that allow the aforementioned movement may be used within the scope of the invention.

The movement provided by hinge 24 and pivot point 26 may likewise be accomplished by a single mechanism or similarly a plurality of mechanisms. Any such arrangement is recognized as falling within the scope of this invention.

Significantly, the heel of the user is shown in FIG. 1 through an open area of the foot boot 90. Increased depth of the heel portion 22 provides spacing of the heel from the device 10 to relieve pressure thereon, thus reducing the risk of heel sores and the like.

The upright 20 is preferably formed of aluminum. However, any lightweight material known to these skilled in the art will be encompassed by the present invention. Moreover, the upright 20 may be formed and contoured according to any suitable method of manufacture.

It should be noted that the straps 60 and 62 may be either elastic or non-elastic in nature. Any such determination in this regard will depend on the need of the patient. Moreover, attachment of the straps 60 and 62 to the calf plate 30 (more particularly described below) and the leverage bars 120 and 122 may be by any known technique including screw, rivet, or snap arrangements.

Referring now to FIGS. 1b and 2a, the calf plate 30 is preferably adjustably connected to calf section 21. Calf plate slide attachment mechanism, or assembly, 34 is fixedly attached to the back of calf plate 30 and has large screws 35 attached thereto to provide slidable movement of the calf plate 30 in slot 36 of the calf section 21, in preferred operation, as well as fixed attachment when the screws are tightened, if desired by the user. The large screws 35 are sized so the heads thereof are wider than the width of the slot 36 to allow for the slidable attachment. Any suitable mechanism may be used to provide such slidable attachment, however.

The calf plate slide attachment mechanism 34 is advantageous since the articulations of the upright 20 are not aligned with the anatomical axis of rotation of the ankle/foot complex. Consequently, forces are produced that cause distal migration of the entire calf portion of the device. Provision of the mechanism 34 helps prevents binding of the articulations of the device and also prevent unnecessary limitations of dorsiflexion and plantar flexion capabilities.

Additionally, as shown in FIGS. 1b and 2a–2c, the calf plate 30 is substantially rectangular in shape, having tapered sides and being provided with a trough 31 for adjustably receiving and retaining the proximal end of the calf section 21 of the upright 20 if the slide attachment mechanism 34 is not used. When the mechanism 34 is provided, the backside of the plate 30 aligned with the trough 31 advantageously provides a flatter surface upon which mechanism 34 is mounted. It is recognized that the calf section 21 may be attached to the calf plate 30 via any known means to provide slidable attachment or otherwise including screws, rivets, friction fit, . . . etc. It is further appreciated that the calf plate 30 is also contoured to conform to the curve of the human calf as illustrated in FIG. 2c.

The calf plate 30 is provided with openings 32 and 33. Such openings facilitate attachment of hook and loop fastener belt 140 and attachment of straps 60 and 62 to the calf plate 30. The belt 140 effectively secures the calf plate 30 to a patient's calf. The belt 140 and straps 60 and 62 are recognized as being attachable to the calf plate 30 using a suitable screw, rivet, snap, or other known attachment means, in conjunction with the openings 32 and 33.

FIGS. 3a and 3b illustrate the foot plate 40, without the leverage bars 120 and 122 more particularly described in connection with FIGS. 7a and 7b. In the preferred arrangement, the foot plate 40 is substantially oval in shape. Moreover, the foot plate 40 is provided with a trough, or channel, 41 for adjustably receiving and retaining the distal end of the foot section 23 of the upright 20.

Additionally, the foot plate 40 is provided with attachment openings 70, 72, 74 and 76. The openings 70, 72, 74 and 76, in conjunction with any known attachment means including screws, rivets, etc., serve to attach the foot section 23 of the upright 20 to the foot plate 40. Such attachment may also be accomplished with a friction fit if desired.

The openings 70 and 72 are further provided for attachment of the toe extension plate 50, as will be further described with respect to FIGS. 4a and 4b. The opening 70 may additionally facilitate attachment of leverage bars 120 and/or 122, as will be more fully described with respect to FIG. 7a and 7b.

The foot plate 40 is preferably slidably adjusted with respect to the foot portion 23, and secured according to any known method or manner. Such adjustment will consequently vary the size of the device 10 to fit the patient.

FIGS. 4a and b illustrate the toe extension plate 50. The toe extension plate 50 is essentially teardrop in shape and is provided with a slot 52 which corresponds to the attachment openings 70 and 72 of the foot plate 40. Screws (not shown) used in conjunction with the openings 70 and 72 engage the slot 52 to bring the toe extension plate 50 into contact with the foot plate 40. Use of the slot 52, as opposed to further holes, provides convenient adjustability, as will be recognized by one of ordinary skill in the art.

FIGS. 4a and b show that the toe extension plate 50 is provided with soft padding 54. Such padding serves to cushion the bottom of the toes when the device 10 is in use.

The calf plate 30, foot plate 40, and toe extension plate 50 are preferably constructed of thermoplastic resin material. However, any similar lightweight material of sufficient strength is contemplated as falling within the scope of the invention. Moreover, the plates 30, 40 and 50 may be formed and contoured according to any known method of manufacture.

Figure 5:
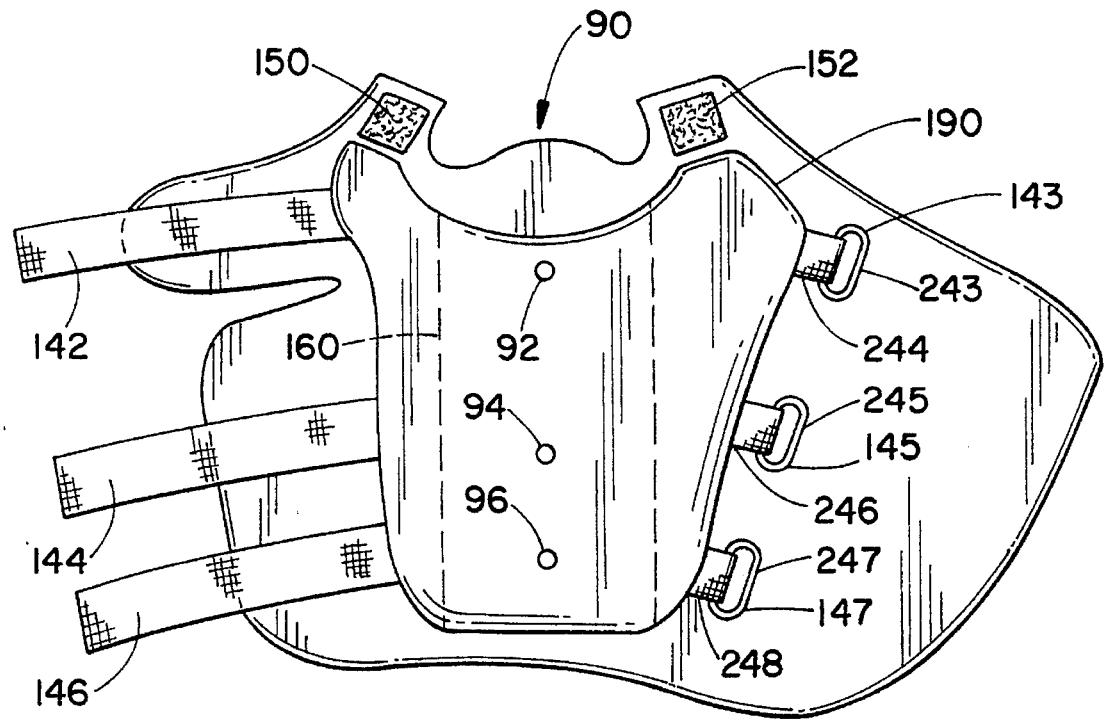
FIG. 5 is a top plan view of the foot boot adaptable for use with the device of FIG. 1.

FIG. 5 illustrates the foot boot 90, in an unused and open state. The foot boot 90 is illustrated in FIG. 5 having a preferred shape to conform to a foot and the device 10 providing both comfort and security. However, any shape which facilitates a comfortable fit and maintenance of the device 10 against the ankle and foot complex may be used.

The foot boot 90 is generally composed of high density lambs wool, or Kodel®, having a hide side and a wool side, and a vinyl pad 190 used for reinforcement. The vinyl pad 190 is preferably a medium weight vinyl or other similar material.

The foot boot 90 includes the hook and loop belts 142, 144 and 146 and corresponding loop members 143, 145 and 147, all of which extend under pad 190 for reinforcement and are sewn, or otherwise attached, thereto. The loop members 143, 145 and 147 comprise approximately 1" wide steel loop portions 243, 245, and 247 through which the belts 142, 144 and 146 are passed and secured. The loop members 143, 145 and 147 further comprise belt portions 244, 246, and 248 of any suitable material that can pass through the loop portions 243, 245 and 247 and be doubled back on itself to be sewn or otherwise secured to effectively anchor the loop members 143, 145, and 147.

Also provided is hook pad 150 corresponding to a loop pad 152. It is appreciated that when the device 10 is in use, the belts 142, 144 and 146 are received through the loop members 143, 145 and 147 and secured and the hook pad 150 is engaged with the loop pad 152 to fasten around outside of upright 20. This arrangement effectively secures the foot boot 90 to a foot and maintains the device 10 against the foot. It is recognized that any suitable arrangement of belts, holes, openings or pads may be utilized in place of the aforenoted arrangement.

The foot boot 90 is further provided with access openings 92, 94 and 96 which are used for attachment to either the foot plate 40 or the toe extension plate 50. Any number of openings or any configuration thereof could also be utilized. Other types of fasteners may also be selectively placed throughout the device 10 to further secure the foot boot 90 therein.

Foot boot 90 is also provided with a pocket 160 (shown in phantom in FIG. 5) to receive the foot plate 40. The pocket 160 in conjunction with suitable fasteners used in connection with openings 92, 94 and 96 provide a secure fit of the foot boot 90 to the foot plate 40.

Figure 6:
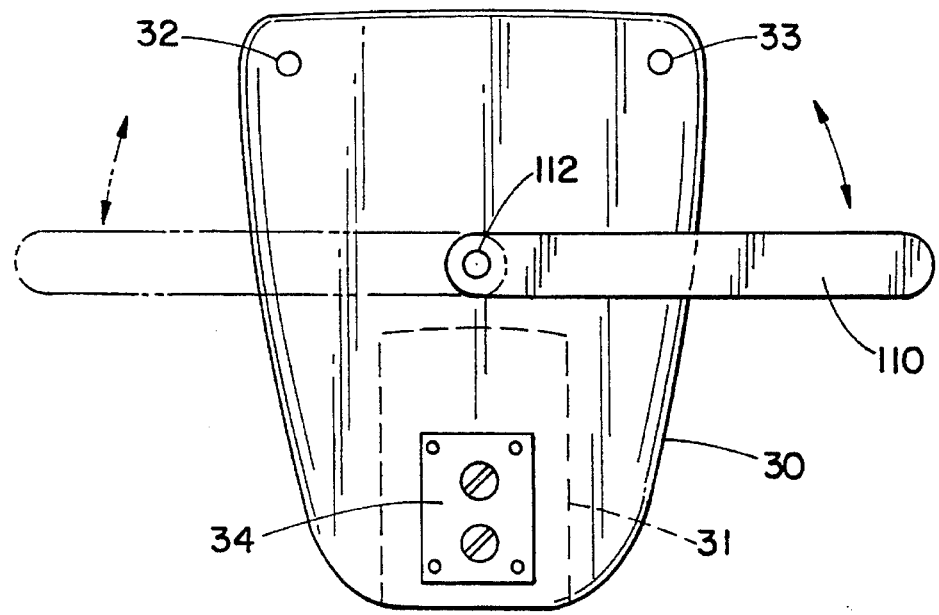
FIG. 6 is a rear elevational view of the calf plate of FIG. 1 incorporating a deroration bar.

As shown in FIG. 6, the calf plate 30 is provided with a derotation bar 110. The derotation bar 110 is pivotally attached to the calf plate 30 at position 112 by any accepted fastening means including screws, rivets, snaps, . . . etc. As indicated by the arrow, the derotation bar 110 can be rotated 180 degrees in order to control rotation of the lower extremity.

Specifically, if a lower extremity of a patient has a tendency to rotate or revolve about the hip in a particular direction, and such rotation is not desirable, the deroration bar 110 is suitably positioned to prevent the rotation. Those of ordinary skill in the art will recognize that the derotation bar 110 may be of any suitable material, including aluminum or plastic, and formed by any conventional technique. Moreover, the derotation bar 110 may vary in configuration and attachment to fit the needs of the users.

Figures 7A, 7B:
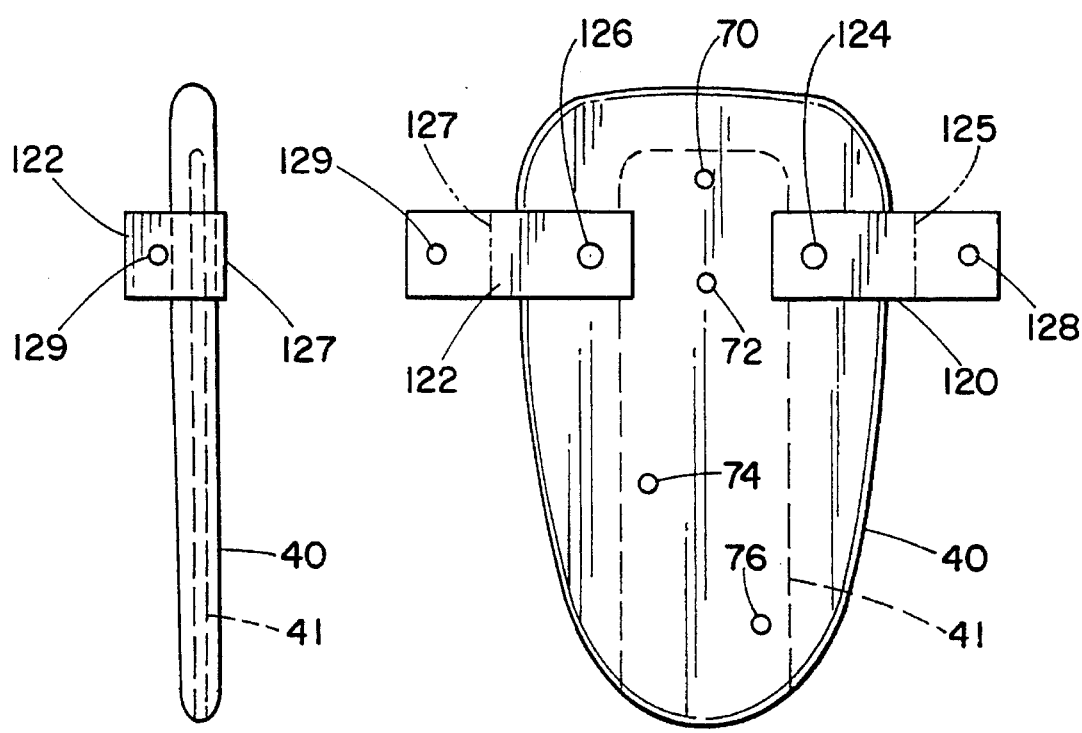

FIGS. 7a and 7b show still a further feature which is preferably incorporated into the present invention. Leverage bars 120 and 122 are provided to the foot plate 40 in order to facilitate attachment of straps 60 and 62. The use of the leverage bars 120 and 122 allow for a more efficient angle of pull of the straps 60 and 62. FIGS. 7a and 7b show that the leverage extension bars 120 and 122 are crimped at an outer end along lines 125 and 127, respectively, and bent approximately 90 degrees for convenient attachment of the straps 60 and 62.

Moreover, as shown in FIGS. 7a and 7b, the bars 120 and 122 are attached to the foot plate 40 at points 124 and 126, respectively, by any known connection means (not shown) including screws, rivets, snaps . . . etc. Attachment points 128 and 129 facilitate attachment of the straps 60 and 62 to the bars 120 and 122.

It is appreciated that the configuration of leverage bars 120 and 122 may be varied. For example, instead of two bars, one leverage bar may be used extending through, or under, the foot plate 40 and secured at any number of points, including a point corresponding to the opening 70 in the foot plate 40. Moreover, the bars may be disposed at various other angles with respect to one another and the foot section 23.

When constructed and in use, as shown in FIG. 1, the device 10 is secured to the ankle and foot complex by wrapping the belt 140, attached to the calf plate 30, around the calf to secure the calf plate 30 thereto. The foot boot 90, suitably wrapped around and attached to the foot portion 23 and foot plate 40, is secured to the foot using the appropriate straps provided to the foot boot 90. The leverage bars 120 and 122 are attached to the foot plate 40 so that the foot boot 90 lies therebetween.

Additionally, the toe extension plate 50 is attached so that the foot boot 90 and the leverage bars 120 and 122 lie between the foot plate 40 and the toe extension plate 50. It is appreciated, though, that any convenient or suitable configuration of the components of the device 10 contemplated by one skilled in the art and achieving the objects and advantages of the present invention fall within the scope thereof.

In operation, the device 10 provides a number of advantages. Because of the hinge 24 and pivot point 26, it can accommodate, correct, and/or prevent soft tissue contractures related to the ankle and foot complex. The depth of the contour of upright 20 at the heel provides relief from pressure exerted by bedding thus greatly reducing the probability of heel sores, quite common in patient populations that spend significant time in bed. The toe extension plate 50 also provides a means to limit contact of bed sheeting on hypersensitive toes.

Further, the aluminum upright 20 less the calf plate 30 can easily be incorporated into a long leg orthosis (KAFO (knee ankle foot orthosis device) or HKAFO (hip knee ankle foot orthosis device)), usually custom molded by those skilled in the art of orthotics.

The orthosis device is preferably provided in "one size fits all" for most applications and neutral respecting either the left or right ankle and foot complex. Additionally, the device 10 is fully adjustable with respect to length at both the calf and foot. The device 10 is also adjustable with respect to desired movement including dorsiflexion, plantar flexion, inversion, eversion, pronation and supination by using the straps 60.

The above description merely provides a disclosure of particular embodiments of the invention and is not intended for the purpose of limiting the same thereto. As such, the invention is not limited to only the above described embodiments. Rather, it is recognized that one skilled in the art could conceive alternative embodiments that fall within the scope of the invention.

Having thus described the invention, I claim:

1. An ankle and foot orthosis device adaptable for use in a human ankle and foot complex to allow movement of a foot having a posterior heel and a toe, the device comprising:
    a calf plate;
    a foot plate; and,
    an upright supporting the calf plate and the foot plate, the upright having a contour portion adapted to conform to the posterior heel of the foot, the contour portion having a hinge for facilitating dorsiflexion and plantar flexion and a pivot point located on the contour portion spaced from the hinge for facilitating inversion, eversion, pronation and supination of the foot.

2. The device according to claim 1 further comprising a toe extension plate adjustably connected to the foot plate, the toe extension plate providing a surface area for placement of the toes.

3. The device according to claim 1 further comprising an enclosable adjustable foot boot attached to the foot plate for securing the device to the ankle and foot complex.

4. The device according to claim 3 wherein the boot comprises a plurality of hook and loop fasteners.

5. The device according to claim 1 further comprising straps connecting the calf plate to the foot plate, first ends of the straps respectively attached to an end of the calf plate and second ends of the straps respectively attached to an end of the foot plate.

6. The device according to claim 5 further comprising leverage bars extending outwardly from the end of the foot plate to facilitate attachment of the second ends of the straps thereto.

7. The device according to claim 1 further comprising a derotation bar connected to the calf plate for controlling rotation of the ankle and foot complex.

8. The device according to claim 1 wherein the upright comprises a substantially L-shaped support having a calf portion connected to the hinge and a foot portion connected at the pivot point.

9. The device according to claim 8 wherein the pivot point comprises a screw.

10. The device according to claim 1 wherein the pivot point comprises a screw inserted in a receiving hole.

11. An ankle and foot orthosis device adaptable for use in a human ankle and foot complex to allow movement of a foot having a posterior heel and a toe, the device comprising:
    a calf plate;
    a foot plate;
    an upright supporting the calf plate and the foot plate, the upright having a contour portion adapted to conform to the posterior heel of the foot, the contour portion having a hinge positioned at an apex of the contour portion for facilitating dorsiflexion and plantar flexion and a pivot point located on the contour portion spaced from the apex for facilitating inversion, eversion, pronation and supination of the foot;

a calf plate slide attachment mechanism slidably attached to the upright and fixedly attached to the calf plate such that the calf plate is slidably adjustable on the upright;

a toe extension plate adjustably connected to the foot plate, the toe extension plate providing a surface area for placement of the toes;

an enclosable adjustable foot boot attached to the foot plate for securing the device to the ankle and foot complex;

straps connecting the calf plate to the foot plate, first ends of the straps respectively attached to an end of the calf plate and second ends of the straps respectively attached to an end of the foot plate;

leverage bars extending outwardly from the end of the foot plate to facilitate attachment of the second ends thereto; and, a derotation bar connected to the calf plate for controlling rotation of the ankle and foot complex.

12. The device according to claim 11 wherein the upright comprises a substantially L-shaped support having a calf portion connected to the hinge and a foot portion connected at the pivot point.

13. The device according to claim 12 wherein the pivot point comprises a screw.

14. The device according to claim 11 wherein the pivot point comprises a screw inserted in a receiving hole.

* * * * *